United States Patent [19]
Wollenberg

[11] Patent Number: 4,645,515
[45] Date of Patent: Feb. 24, 1987

[54] MODIFIED SUCCINIMIDES (II)

[75] Inventor: Robert H. Wollenberg, San Rafael, Calif.

[73] Assignee: Chevron Research Company, San Francisco, Calif.

[21] Appl. No.: 722,883

[22] Filed: Apr. 12, 1985

[51] Int. Cl.$^4$ ............................................. C10L 1/22
[52] U.S. Cl. ........................................... 44/63; 44/70; 44/71; 252/392; 548/537
[58] Field of Search ............... 44/63, 70, 71; 252/392; 548/537

[56] References Cited

U.S. PATENT DOCUMENTS

| 3,458,530 | 7/1969 | Siegel et al. | 44/63 |
| 3,717,446 | 2/1973 | Howland et al. | 44/63 |
| 3,997,569 | 12/1976 | Powell | 44/63 |
| 4,047,899 | 9/1977 | Powell | 44/63 |
| 4,396,399 | 8/1983 | Kaufman et al. | 44/63 |
| 4,482,464 | 11/1984 | Karol et al. | 252/51.5 A |

Primary Examiner—Y. Haris-Smith
Attorney, Agent, or Firm—S. R. LaPaglia; R. C. Gaffney; G. F. Swiss

[57] ABSTRACT

Disclosed are polyamino alkenyl or alkyl succinimides which have been modified by treatment with a lactone to yield polyamino alkenyl or alkyl succinimides wherein one or more of the basic nitrogens of the polyamino moiety is substituted with a hydroxyalkylene carbonyl group. The additives so disclosed are useful as dispersants in lubricating oils, gasolines, marine crankcase oils and hydraulic oils.

11 Claims, No Drawings

MODIFIED SUCCINIMIDES (II)

BACKGROUND OF THE INVENTION

1. Field of the Invention

This invention relates to additives which are useful as dispersants and/or detergents in lubricating oils. In particular, this invention is directed toward polyamino alkenyl or alkyl succinimides which have been modified by treatment with a compound of the formula

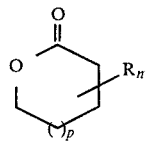

wherein R is alkyl of 1 to 2 carbon atoms; n is an integer of from 0 to 3; and p is an integer equal to 0 or 1. The modified polyamino alkenyl or alkyl succinimides of this invention have been found to possess dispersancy and/or detergency properties in lubricating oil. These modified succinimides are also useful as detergents and/or dispersants in fuels.

2. Prior Art

Alkenyl or alkyl succinimides have been previously modified with hydroxy alkylene acids selected from glycolic, lactic, 2-hydroxymethylpropionic and 2,2'-bis-hydroxymethylpropionic acids. These modified succinimides are taught as dispersant additives for lubricating oils (see Karol et al., U.S. Pat. No. 4,482,464). However, there is no teaching in these patents, or apparently elsewhere, to modify alkenyl or alkyl succinimides with the lactones employed in this invention.

SUMMARY OF THE INVENTION

It has now been found that polyamino alkenyl or alkyl succinimides may be modified by reaction with a lactone of the formula:

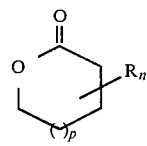

wherein R is alkyl of from 1 to 2 carbon atoms; n is an integer of from 0 to 3; and p is an integer of from 0 to 1. The lactone reacts with the polyamino alkenyl or alkyl succinimide by converting a primary or secondary amine of the polyamino moiety to a hydroxyalkyleneamide. Accordingly, the present invention relates to a polyamino alkenyl or alkyl succinimide wherein one or more of the nitrogens of the polyamino moiety is substituted with a hydroxyalkylene carbonyl wherein said alkylene is a three or four carbon alkylene group or a three or four carbon alkylene group substituted with from 1 to 3 alkyl groups of from 1 to 2 carbons each.

As noted above, the modified polyamino alkenyl or alkyl succinimides of this invention possess dispersancy and/or detergency properties when used in either lubricating oils or fuels. Thus, another aspect of this invention is a lubricating oil composition comprising a major amount of an oil of lubricating viscosity and an amount of a modified polyamino alkyl or alkenyl succinimide of this invention sufficient to provide dispersancy and/or detergency.

In another aspect of this invention is a fuel composition comprising a major portion of a hydrocarbon boiling in a gasoline range and an amount of a modified polyamino alkyl or alkenyl succinimide of this invention sufficient to provide dispersancy and/or detergency.

In general, the alkenyl or alkyl group of the succinimide is from 10 to 300 carbon atoms. While the modified succinimides of this invention possess good detergency properties even for alkenyl or alkyl groups of less than 20 carbon atoms, dispersancy is enhanced when the alkenyl or alkyl group is at least 20 carbon atoms. Accordingly, in a preferred embodiment, the alkenyl or alkyl group of the succinimide is at least 20 carbon atoms.

Still another aspect of the instant invention is a process for preparing polyamino alkenyl or alkyl succinimides wherein one or more of the nitrogens of the polyamino moiety is substituted with a hydroxyalkylene carbonyl group wherein said alkylene is a 3 or 4 carbon alkylene optionally substituted with from 1 to 3 alkyl groups of 1 to 2 carbons each; which comprises contacting at a temperature sufficient to cause reaction a lactone of Formula I with a polyamino alkenyl or alkyl succinimide.

The process of this invention is particularly advantageous in that water is not formed during the reaction. In general, excess water, 1% or more, in the succinimide is detrimental and generally undesirable resulting in increased engine corrosion if not removed prior to formulation in the lubricating oil package. Accordingly, excess water should be removed prior to formulation. Moreover, glycolic acid as employed in Karol et al. is an aqueous solution which result in much greater amounts of water which must be removed. Accordingly, by using the process of the instant invention, water either internally formed or externally added is avoided.

DETAILED DESCRIPTION OF THE INVENTION

The modified polyamino alkenyl or alkyl succinimides of this invention are prepared by reaction of a polyamino alkenyl or alkyl succinimide with a lactone of formula I above. The reaction is conducted at a temperature sufficient to cause reaction of the lactone with the polyamino alkenyl or alkyl succinimide. In particular, reaction temperatures of from about 0° C. to about 250° C. are preferred with temperatures of from about 100° C. to 200° C. being more preferred.

The reaction may be conducted neat—that is, both the polyamino alkenyl or alkyl succinimide and the lactone are combined in the proper ratio, either alone or in the presence of a catalyst, such as an acidic, basic or Lewis acid catalyst, and then stirred at the reaction temperature. Examples of suitable catalysts include, for instance, boron trifluoride, alkane sulfonic acid, alkali or alkaline carbonate.

Alternatively, the reaction may be conducted in a diluent. For example, the reactants may be combined in a solvent such as toluene, xylene, oil or the like, and then stirred at the reaction temperature. After reaction completion, volatile components may be stripped off. When a diluent is employed, it is preferably inert to the reactants and products formed and is generally used in an amount sufficient to insure efficient stirring.

Water, which can be present in the polyamino alkenyl or alkyl succinimide generally at about 0.5%, can be removed from the reaction system before the reaction via azeotroping or distillation. After reaction completion, the system can be stripped at elevated temperatures (100° C. to 250° C.) and reduced pressures to remove any volatile components which may be present in the product.

Another embodiment of the above process is a continuous flow system in which the polyamino alkenyl or alkyl succinic anhydride and polyamine are added at the front end of the flow while the lactone is added further downstream in the system.

Mole charge of the lactone to the basic amine nitrogen of the polyamino alkenyl or alkyl succinimide employed in the process of this invention are generally in the range of from about 0.2:1 to about 1:1, although preferably from about 0.5:1 to about 1:1 and most preferably from about 0.7:1 to about 1:1.

As used herein, the term "molar charge" of lactone to the basic nitrogen of a polyamino alkenyl or alkyl-succinimide" means that the molar charge of lactone employed in the reaction is based upon the theoretical number of basic nitrogens contained in the succinimide. Thus, when 1 equivalent of triethylene tetraamine (TETA) is reacted with an equivalent of succinic anhydride, the resulting monosuccinimide will theoretically contain 3 basic nitrogens. Accordingly, a molar charge of 1 would require that a mole of lactone be added for each basic nitrogen or in this case 3 moles of lactone for each mole of monosuccinimide prepared from TETA.

The reaction is generally complete from within 0.5 to 10 hours.

A. ALKENYL OR ALKYL SUCCINIMIDES

The polyamino alkenyl or alkyl succinimides that can be used to prepare the lubricating oil additives described herein are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746, the disclosures of which are hereby incorporated by reference. The term "succinimide" is understood in the art to include many of the amide, imide and amidine species which are also formed by this reaction. The predominant product however is succinimide and this term has been generally accepted as meaning the product of a reaction of an alkenyl substituted succinic acid or anhydride with a polyamine. As used herein, included within this term are the alkenyl or alkyl mono-, bis-succinimides and other higher analogs.

A(1) Succinic Anhydride

The preparation of the alkenyl-substituted succinic anhydride by reaction with a polyolefin and maleic anhydride has been described, e.g., U.S. Pat. Nos. 3,018,250 and 3,024,195. Such methods include the thermal reaction of the polyolefin with maleic anhydride and the reaction of a halogenated polyolefin, such as a chlorinated polyolefin, with maleic anhydride. Reduction of the alkenyl-substituted succinic anhydride yields the corresponding alkyl derivative. Alternatively, the alkenyl substituted succinic anhydride may be prepared as described in U.S. Pat. Nos. 4,388,471 and 4,450,281 which are totally incorporated herein by reference.

Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of 2 or more such olefins such as copolymers of: ethylene and propylene, butylene, and isobutylene, etc. Other copolymers include those in which a minor amount of the copolymer monomers, e.g., 1 to 20 mole percent is a $C_4$ to $C_8$ non-conjugated diolefin, e.g., a copolymer of isobutylene and butadiene or a copolymer of ethylene, propylene and 1,4-hexadiene, etc.

The polyolefin polymer usually contains from about 10 to 300 carbon atoms, although preferably 10 to 200 carbon atoms more preferably 12 to 100 carbon atoms and most preferably 20 to 100 carbon atoms.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

In addition to the reaction of a polyolefin with maleic anhydride, many other alkylating hydrocarbons may likewise be used with maleic anhydride to produce alkenyl succinic anhydride. Other suitable alkylating hydrocarbons include cyclic, linear, branched and internal or alpha olefins with molecular weights in the range 100–4,500 or more with molecular weights in the range of 200–2,000 being more preferred. For example, alpha olefins obtained from the thermal cracking of paraffin wax. Generally, these olefins range from 5–20 carbon atoms in length. Another source of alpha olefins is the ethylene growth process which gives even number carbon olefins. Another source of olefins is by the dimerization of alpha olefins over an appropriate catalyst such as the well known Ziegler catalyst. Internal olefins are easily obtained by the isomerization of alpha olefins over a suitable catalyst such as silica.

A(2) Polyamine

The polyamine employed to prepare the alkenyl or alkyl succinimides is preferably a polyamine having from 2 to about 12 amine nitrogen atoms and from 2 to about 40 carbon atoms. The polyamine is reacted with an alkenyl or alkyl succinic anhydride to produce the polyamino alkenyl or alkyl succinimide, employed in this invention. The polyamine is so selected so as to provide at least one basic amine per succinimide. Since the reaction of the polyamino alkenyl or alkyl succinimide with the lactones employed in this invention is believed to proceed through a secondary or primary amine, at least one of the basic amine atoms of the alkenyl or alkyl succinimide must either be a primary amine or a secondary amine. Accordingly, in those instances in which the succinimide contains only one basic amine, that amine must either be a primary amine or a secondary amine. The polyamine preferably has a carbon-to-nitrogen ratio of from about 1:1 to about 10:1.

The polyamine portion of the polyamino alkenyl or alkyl succinimide may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms. At least one of the substituents on one of the amines of the polyamine is hydrogen, e.g., at least one of the basic nitrogen atoms of the polyamine is a primary or secondary amino nitrogen atom.

Hydrocarbyl, as used in describing the polyamine components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-[2-(2-ethoxyethoxy)ethoxy]ethyl, 3,6,9,12-tetraoxatetradecyl, 2-(2-ethoxyethoxy)hexyl, etc. The acyl groups of the aforementioned (C) substituents are such as propionyl, acetyl, etc. The more preferred substituents are hydrogen, $C_1$-$C_6$ alkyls and $C_1$-$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, 1,3,2-hydroxypropylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydroxy- and hydrocarbyl-substituted polyamines. Among the polyalkylene polyamines, those containing 2-12 amine nitrogen atoms and 2-24 carbon atoms are especially preferred, and the $C_2$-$C_5$ alkylene polyamines are most preferred, in particular, the lower polyalkylene polyamines, e.g., ethylene diamine, dipropylene triamine, etc.

The polyamine component also may contain heterocyclic polyamines, heterocyclic substituted amines and substituted heterocyclic compounds, wherein the heterocycle comprises one or more 5-6 membered rings containing oxygen and/or nitrogen. Such heterocycles may be saturated or unsaturated and substituted with groups selected from the aforementioned (A), (B), (C) and (D). The heterocycles are exemplified by piperazines, such as 2-methylpiperazine, N-(2-hydroxyethyl)-piperazine, 1,2-bis-(N-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)-mortpholine, etc. Among the heterocyclic compounds, the piperazines are preferred.

Typical polyamines that can be used to form the compounds of this invention include the following: ethylene diamine, 1,2-propylene diamine, 1,3-propylene diamine, diethylene triamine, triethylene tetramine, hexamethylene diamine, tetraethylene pentamine, methylaminopropylene diamine, N-(betaaminoethyl)piperazine, N,N'-di(betaaminoethyl)piperazine, N,N'-di(beta-aminoethyl)-imidazolidone-2, N-(beta-cyanoethyl)ethane-1,2-diamine, 1,3,6,9-tetraaminooctadecane, 1,3,6-triamino-9-oxadecane, N-(beta-aminoethyl)diethanolamine, N-methyl-1,2-propanediamine, N-(betanitroethyl)-1,3-propane diamine, 2-(2-aminoethylamino)-ethanol,2-[2-(2-aminoethylamino)-ethylamino]-ethanol.

Another group of suitable polyamines are the propyleneamines, (bisaminopropylethylenediamines). Propyleneamines are prepared by the reaction of acrylonitrile with an ethyleneamine, for example, an ethyleneamine having the formula $H_2N(CH_2CH_2NH)_ZH$ wherein Z is an integer from 1 to 5, followed by hydrogenation of the resultant intermediate. Thus, the product prepared from ethylene diamine and acylonitrile would be $H_2N(CH_2)_3NH(CH_2)_2NH(CH_2)_3NH_2$.

In many instances the polyamine used as a reactant in the production of succinimides of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be largely tetraethylene pentamine and the empirical formula of the total amine composition will closely approximate that of tetraethylene pentamine. Finally, in preparing the succinimide for use in this invention, where the various nitrogen atoms of the polyamine are not geometrically equivalent, several substitutional isomers are possible and are encompassed within the final product. Methods of preparation of polyamines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volumes 2, pp. 99-116.

The reaction of a polyamine with an alkenyl or alkyl succinic anhydride to produce the alkenyl or alkyl succinimides is well known in the art and is disclosed in U.S. Pat. Nos. 2,992,708; 3,018,291; 3,024,237;

3,100,673; 3,219,666; 3,172,892 and 3,272,746. The above are incorporated herein by reference for their disclosures of preparing alkenyl or alkyl succinimides.

As noted above, the term "polyamino alkenyl or alkyl succinimide" refers to both the mono- and bis-succinimides and to the higher analogs of polyamino alkenyl or alkyl poly succinimides. Preparation of the bis- and higher analogs may be accomplished by controlling the molar ratio of the reagents. For example, a product comprising predominantly mono- or bis-succinimide can be prepared by controlling the molar ratios of the polyamine and succinic anhydride. Thus, if one mole of polyamine is reacted with one mole of an alkenyl or alkyl substituted succinic anhydride, a predominantly mono-succinimide product will be prepared. If two moles of an alkenyl or alkyl substituted succinic anhydride are reacted per mole of polyamine, a bis-succinimide is prepared. Higher analogs may likewise be prepared.

A particularly preferred class of polyamino alkenyl or alkyl succinimides employed in the process of the instant invention may be represented by Formula II:

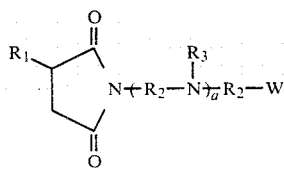

wherein $R_1$ is alkenyl or alkyl of from 10 to 300 carbon atoms; $R_2$ is alkylene of 2 to 10 carbon atoms; $R_3$ is hydrogen or lower alkyl of from 1 to 6 carbon atoms; a is an integer from 0 to 10; and W is —$NH_2$ or represents a group of Formula III:

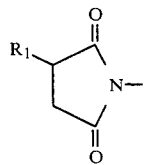

wherein $R_1$ is alkenyl or alkyl of from 10 to 300 carbon atoms; with the proviso that when W is the group of Formula III above, than a is not zero and at least one of $R_3$ is hydrogen.

The polyamino alkenyl or alkyl succinimides of Formula II above are generally prepared from the reaction of an alkylene polyamine with an alkenyl or alkyl succinic anhydride.

In Formula II, the polyamino alkenyl or alkyl succinimides may be conveniently viewed as being composed of three moieties that is the alkenyl or alkyl moiety R, the succinimide moiety represented by the formula:

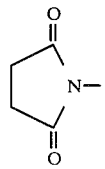

and the polyamino moiety represented by the group

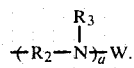

As indicated above, the polyamine employed in preparing the succinimide is often a mixture of different compounds having an average composition indicated as in Formula IV below:

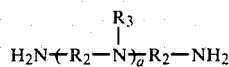

wherein $R_2$, $R_3$ and a are as defined above. Accordingly, in Formula IV each value of $R_2$ and a may be the same or different from other values of $R_2$ and a. Moreover, cyclic heterocycles, such as piprazine, may be included to some extent in the alkylene diamines, IV.

Preferably, $R_2$ is alkylene of 2 to 6 carbon atoms and most preferably is either ethylene or propylene.

Preferably, $R_3$ is hydrogen while a is preferably an integer from 1 to 6.

B. LACTONES

The lactones employed in this invention may be represented by the formula:

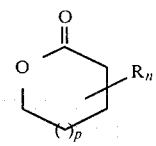

wherein R is alkyl of from 1 to 2 carbon atoms; n is an integer of from 0 to 3; and p is an integer of from 0 to 1. Preferably, n is equal to either 0 or 1 while R is preferably methyl. Most preferably, n is zero.

The lactones of Formula I above are either commercially available such as gamma butyrolactone and delta valerolactone or may be prepared by art recognized procedures such as those disclosed in U.S. Pat. No. 4,309,352 and by Christian et al., "Journal American Chemical Society", 69, 1961–1963 (1947).

Lactones which may be employed in this invention include, for instance, gamma butyrolactone, gamma valerolactone(tetrahydro-5-methyl-2-furanone), delta valerolactone, tetrahydro-5,5-dimethyl-2-furanone, 6-methyl delta valerolactone, 6-ethyl delta valerolactone, and the like.

C. MODIFIED SUCCINIMIDE COMPLEXES

The lactones of this invention react with primary and secondary amines of a polyamino alkenyl or alkyl succinimide to form hydroxyalkylene amides. This is illustrated in reaction (1) below which employs gamma butyrolactone for illustrative purposes. It is understood that other lactones of Formula I react similarly.

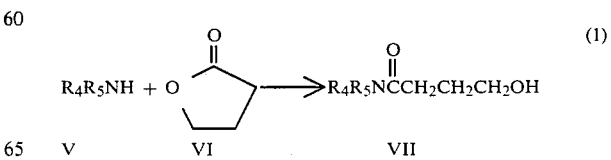

wherein $R_4$ and $R_5$ form the remainder of a polyamino alkenyl or alkyl succinimide. In this reaction, the amine nitrogen has been rendered nonbasic by formation of the amide VII.

If additional lactone is added to the reaction, it will react with any available primary or secondary amine of the polyamino alkenyl or alkyl succinimide and convert these to hydroxyalkylene amides. Preferably, it is desirable to convert as many of the primary and secondary amines to amides.

However, as previously noted, alkylene polyamines such as triethylene tetraamine and tetraethylene pentaamine contain tertiary amines (piperazines, etc.), which may account for as much as 30% of the basic nitrogen content. Although Applicant does not want to be limited to any theory, it is believed that these tertiary amines, although basic, are not reactive with the lactone. Accordingly, maximum hydroxyalkylene amide content in the polyamino alkenyl or alkyl succinimide can be obtained by employing a molar charge of lactone to the basic nitrogen of the alkenyl or alkyl succinimide of from 0.7:1 to about 1:1. In some cases, a slight excess of lactone may be employed to enhance reaction rate.

A preferred embodiment of the present invention comprises a compound of the formula:

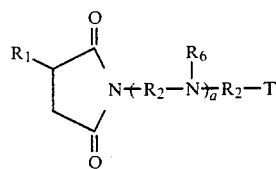

wherein $R_1$ is alkenyl or alkyl of from 10 to 300 carbon atoms; $R_2$ is alkylene of 2 to 10 carbon atoms; $R_6$ is hydrogen, lower alkyl of from 1 to 6 carbon atoms, and hydroxyalkylene carbonyl wherein said alkylene is a three or four carbon alkylene group or a three or four carbon alkylene group substituted with from 1 to 3 alkyl groups of from 1 to 2 carbon atoms each; a is an integer of from 0 to 10; and W is —NH$_2$,

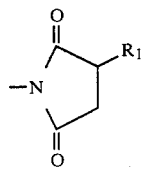

wherein $R_1$ is alkenyl or alkyl of from 10 to 300 carbon atoms and hydroxyalkyleneamido (HO alkylene

wherein said alkylene is a three or four carbon alkylene group or a three or four carbon alkylene group substituted with from 1 to 3 alkyl groups of from 1 to 2 carbon atoms each with the proviso that if T is either —NH$_2$ or

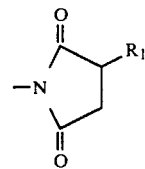

then a is not zero and at at least one of $R_6$ is hydroxyalkylene carbonyl.

The modified polyamino alkenyl or alkyl succinimides of this invention can be reacted with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to 10 equivalents of boron compound to the modified succinimide may be employed.

The modified polyamino alkenyl or alkyl succinimides of this invention are useful as detergent and dispersant additives when employed in lubricating oils. When employed in this manner, the modified polyamino alkenyl or alkyl succinimide additive is usually present in from 0.2 to 10 percent by weight to the total composition and preferably at about 0.5 to 5 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. (−18° C.) to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions.

Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

It is also contemplated the modified succinimides of this invention may be employed as dispersants and detergents in hydraulic fluids, marine crankcase lubricants and the like. When so employed, the modified succinimide is added at from about 0.1 to 10 percent by weight to the oil. Preferably, at from 0.5 to 5 weight percent.

When used in fuels, the proper concentration of the additive necessary in order to achieve the desired detergency is dependent upon a variety of factors including the type of fuel used, the presence of other detergents or dispersants or other additives, etc. Generally, however, and in the preferred embodiment, the range of concentration of the additive in the base fuel is 10 to 10,000 weight parts per million, preferably from 30 to 2,000 weight parts per million, and most preferably from 30 to 700 parts per million of the modified succinimide per part of base fuel. If other detergents are present, a lesser amount of the modified succinimide may be used.

The modified succinimide additives of this invention may be formulated as a fuel concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will be ordinarily at least 10 percent by weight and generally not exceed 70 percent by weight and preferably from 10 to 25 weight percent.

The following examples are offered to specifically illustrate this invention. These examples and illustrations are not to be construed in any way as limiting the scope of this invention.

EXAMPLES

Example 1

To a 500 ml reaction flask was charged 253.4 g of a succinimide dispersant composition [prepared from 1 mole of polyisobutenyl succinic anhydride (where the polyisobutenyl group has a number average molecular weight of 950) and 0.9 mole of triethylene-tetraamine and which consists of about 50% lubricating oil diluent and having alkalinity value (AV) of 47 mg KOH/g]. To this succinimide was added 25.8 g gamma butyrolactone. The mixture was heated to 150±5° C. for 3 hrs. Recovered 262 g product containing 2.16% N and having an AV=31.3 mg KOH/g.

Example 2

To a 5 liter reaction flask was charged 2534. g of the succinimide dispersant composition of Example 1 and 258. g delta butyrolactone. The reaction mixture was stirred and heated at 150±5° C. for 9 hrs. Recovered 2755 g product containing 2.15% N and having an AV=25.8.

Example 3

To a 500 ml reaction flask was charged 126.7 g of the succinimide dispersant composition of Example 1 and 25.8 g delta butyrolactone. The reaction mixture was stirred and heated at 150±5° C. for 9 hrs. Recovered 139 g product containing 2.16% N and having an AV=27.3.

Likewise, by following the procedures in the above examples, the following lactones may be substituted for gamma butyrolactone to yield modified succinimides useful in this invention: tetrahydro-5-methyl-2-furanone, delta valerlactone, tetrahydro-5,5-dimethyl-2-furanone, 6-methyl delta valerolactone and 6-ethyl delta valerolactone.

Example 4

Formulated oil containing a modified succinimide of the invention was tested in a Sequence V-D Test method (according to candidate test for ASTM). This procedure utilizes a Ford 2.3-liter, four-cylinder Pinto engine. The test method simulates a type of severe field test service characterized by a combination of low speed, low temperature "stop and go" city driving and moderate turnpike operation. The effectiveness of the additives in the oil is measured in terms of the protection against sludge and varnish deposits on a 0 to 10 scale with 0 being black and 10 indicating no varnish or sludge deposits. The result are indicated in Table I.

The comparisons were made in a formulated oil Exxon 150N 10W40 containing a succinimide dispersant, 20 mmoles/ka Ca as an overbased calcium phenate, 30 mmoles/kg Ca as an overbased calcium sulfonate, 0.16% zinc as primary alkyl zinc dithiophosphate, and a nondispersant ethylene-propylene copolymer VI improver to give an SAE 10W40 oil.

TABLE I

| Formulation Contained 6% Succinimide of Example[1] | Mean of No. of Tests | Average Varnish | Piston Varnish | Average Sludge |
|---|---|---|---|---|
| Starting succinimide of Example 2 | 5 | 5.1 | 6.7 | 9.6 |
| Example | 2 | 6.5 | 7.3 | 9.5 |

[1]Succinimide in the Examples is in 50% diluent oil which results in a 3% concentration of actives.

What is claimed is:

1. A polyamino alkenyl or alkyl succinimide wherein one or more of the nitrogens of the polyamino moiety is substituted with hydroxyalkylene carbonyl wherein said alkylene is a three or four carbon alkylene group or a three or four carbon alkylene group substituted with from 1 to 3 alkyl groups of from 1 to 2 carbons each.

2. The polyamino alkenyl or alkyl succinimide of claim 1 wherein said alkylene is a three or four carbon alkylene group and said alkenyl or alkyl is a $C_{20}$–$C_{100}$ alkenyl or alkyl group.

3. The polyamino alkenyl or alkyl succinimide of claim 2 wherein said alkylene is propylene.

4. The polyamino alkenyl or alkyl succinimide of claim 2 wherein said alkylene is butylene.

5. The polyamino alkenyl or alkyl succinimide of claim 1 wherein said alkylene is a three or four carbon alkylene group substituted with from 1 to 3 alkyl groups of from 1 to 2 carbons each.

6. The polyamino alkenyl or alkyl succinimide of claim 1 wherein said hydroxyalkylene carbonyl is hydroxy(3-methyl)propylene carbonyl (i.e.,

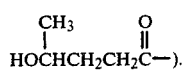

7. A compound of the formula:

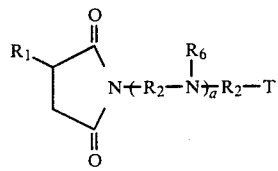

wherein $R_1$ is alkenyl or alkyl of from 10 to 300 carbon atoms; $R_2$ is alkylene of 2 to 10 carbon atoms; $R_6$ is hydrogen, lower alkyl of from 1 to 6 carbon atoms, and hydroxyalkylene carbonyl wherein said alkylene is a three or four carbon alkylene group or a three or four carbon alkylene group substituted with from 1 to 3 alkyl groups of from 1 to 2 carbon atoms each; a is an integer of from 0 to 10; and T is —NH$_2$,

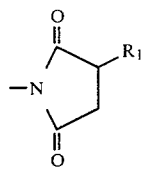

wherein $R_1$ is alkenyl or alkyl of from 10 to 300 carbon atoms, and hydroxyalkyleneamide wherein said alkylene is a three or four carbon alkylene group or a three or four carbon alkylene group substituted with from 1 to 3 alkyl groups of from 1 to 2 carbon atoms each with the proviso that if T is either —NH$_2$ or

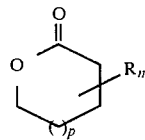

then a is not zero and at at least one of $R_6$ is hydroxyalkylene carbonyl.

8. A fuel composition comprising a hydrocarbon boiling in the gasoline range and from 10 to 10,000 parts per million of a compound as defined in any of claims 1 and 7.

9. A fuel concentrate comprising 30 to 90 weight percent of an inert stable oleophilic organic solvent and 10 to 70 weight percent of a compound as defined in any of claims 1 and 7.

10. A process for preparing a polyamino alkenyl or alkyl succinimides wherein one or more of the basic nitrogens of the polyamino moiety is substituted with a hydroxyalkylene carbonyl group wherein said alkylene is a 3 or 4 carbon alkylene group or a 3 or 4 carbon alkylene group substituted with 1 to 3 alkyl groups of 1 to 2 carbons each which comprises contacting a temperature sufficient to cause reaction a lactone represented by the formula

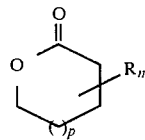

wherein R is alkyl of from 1 to 2 carbon atoms; n is an integer from 0 to 3; and p is an integer of from 0 to 1; with a polyamino alkenyl or alkyl succinimide.

11. The process as defined in claim 10 wherein the process is conducted at from 0° to 250° C.

* * * * *